(12) United States Patent
Meyer

(10) Patent No.: US 8,399,731 B2
(45) Date of Patent: Mar. 19, 2013

(54) PHOTOTHERAPY WOUND TREATMENT

(75) Inventor: Peter F. Meyer, Shrewsbury, MA (US)

(73) Assignee: Covidien LP, Mansfield, MA (US)

( * ) Notice: Subject to any disclaimer, the term of this patent is extended or adjusted under 35 U.S.C. 154(b) by 288 days.

(21) Appl. No.: 12/407,565

(22) Filed: Mar. 19, 2009

(65) Prior Publication Data

US 2010/0241196 A1 Sep. 23, 2010

(51) Int. Cl.
*A61F 13/00* (2006.01)
(52) U.S. Cl. .................. 602/54; 602/2; 602/41; 607/88; 607/91
(58) Field of Classification Search .......... 602/2, 41–59; 607/88–94; 359/572
See application file for complete search history.

(56) References Cited

U.S. PATENT DOCUMENTS

| | | | |
|---|---|---|---|
| 4,574,338 A * | 3/1986 | Takasaki et al. ............... 362/278 |
| 4,690,141 A * | 9/1987 | Castel et al. .................... 607/90 |
| 4,726,364 A | 2/1988 | Wylan |
| 4,898,438 A | 2/1990 | Mori |
| 4,909,254 A | 3/1990 | Wilkinson |
| 4,996,046 A | 2/1991 | Warshaw et al. |
| 5,010,452 A | 4/1991 | Krebser et al. |
| 5,441,531 A | 8/1995 | Zarate et al. |
| 5,833,683 A | 11/1998 | Fuller et al. |
| 5,968,033 A | 10/1999 | Fuller et al. |
| 6,063,108 A | 5/2000 | Salansky et al. |
| 6,096,066 A * | 8/2000 | Chen et al. ....................... 607/88 |
| 6,406,474 B1 | 6/2002 | Neuberger et al. |
| 6,533,803 B2 | 3/2003 | Babaev |
| 6,645,230 B2 | 11/2003 | Whitehurst |
| 6,660,000 B2 | 12/2003 | Neuberger et al. |
| 6,730,113 B2 | 5/2004 | Eckhardt et al. |
| 6,843,778 B2 | 1/2005 | Foldes |
| 6,997,923 B2 * | 2/2006 | Anderson et al. .................. 606/9 |
| 7,052,167 B2 | 5/2006 | Vanderschuit |
| 7,210,817 B2 * | 5/2007 | Lee et al. ................. 362/249.04 |
| 7,282,060 B2 | 10/2007 | DeBenedictis et al. |
| 7,304,201 B2 * | 12/2007 | Holloway et al. ............... 602/41 |
| 7,323,614 B2 | 1/2008 | Lerat et al. |
| 7,351,252 B2 | 4/2008 | Altshuler et al. |
| 8,246,666 B2 * | 8/2012 | Pressler et al. ................... 607/88 |
| 2001/0050083 A1 * | 12/2001 | Marchitto et al. ............ 128/898 |
| 2003/0114884 A1 | 6/2003 | Moran |
| 2004/0034398 A1 | 2/2004 | Eckhardt et al. |
| 2004/0133143 A1 * | 7/2004 | Burton et al. .................... 602/58 |
| 2005/0038418 A1 | 2/2005 | Altshuler et al. |
| 2005/0049582 A1 * | 3/2005 | DeBenedictis et al. ........... 606/9 |
| 2005/0049658 A1 | 3/2005 | Connors et al. |
| 2005/0080465 A1 | 4/2005 | Zelickson et al. |
| 2006/0122668 A1 | 6/2006 | Anderson et al. |
| 2006/0167532 A1 | 7/2006 | Parker |

(Continued)

OTHER PUBLICATIONS

Notification of Transmittal of The International Search Report and the Written Opinion of the International Searching Authority, or the Declaration dated May 7, 2010.

*Primary Examiner* — Nicholas Lucchesi
*Assistant Examiner* — Kari Petrik

(57) ABSTRACT

A wound treatment for use during phototherapy treatment of a wound includes a pliable optical component adapted to be applied over the wound and to direct light rays during phototherapy treatment, and a bandage for securing the Fresnel lens over the wound. The optical component may be configured to direct light rays toward a perimeter edge of the wound. A wound treatment kit for phototherapy treatment of a wound includes a package and a sterile, pliable optical component in the package. The optical component is removable from the sterile package and is placed over the wound during the phototherapy treatment. The optical component directs light rays toward a selected area of the wound during phototherapy treatment.

7 Claims, 9 Drawing Sheets

U.S. PATENT DOCUMENTS

| | | |
|---|---|---|
| 2006/0173514 A1 | 8/2006 | Biel et al. |
| 2006/0217787 A1* | 9/2006 | Olson et al. .................... 607/88 |
| 2006/0282028 A1 | 12/2006 | Howard et al. |
| 2006/0293727 A1 | 12/2006 | Spooner et al. |
| 2007/0021807 A1 | 1/2007 | Kurtz |
| 2007/0203442 A1 | 8/2007 | Bechert et al. |
| 2007/0208395 A1 | 9/2007 | LeClerc et al. |
| 2007/0239146 A1 | 10/2007 | Wang |
| 2007/0282402 A1 | 12/2007 | Irwin |
| 2008/0009842 A1 | 1/2008 | Manstein et al. |
| 2008/0033514 A1 | 2/2008 | Kurtz |
| 2008/0033515 A1 | 2/2008 | Kurtz |
| 2008/0033516 A1 | 2/2008 | Altshuler et al. |
| 2008/0058689 A1 | 3/2008 | Holloway et al. |
| 2008/0058907 A1 | 3/2008 | Reuben |
| 2008/0103558 A1 | 5/2008 | Wenzel et al. |
| 2009/0112295 A1* | 4/2009 | Hyde et al. ...................... 607/88 |
| 2009/0204109 A1* | 8/2009 | Grove et al. ...................... 606/9 |
| 2012/0265120 A1* | 10/2012 | Beisang et al. ................ 604/20 |

* cited by examiner

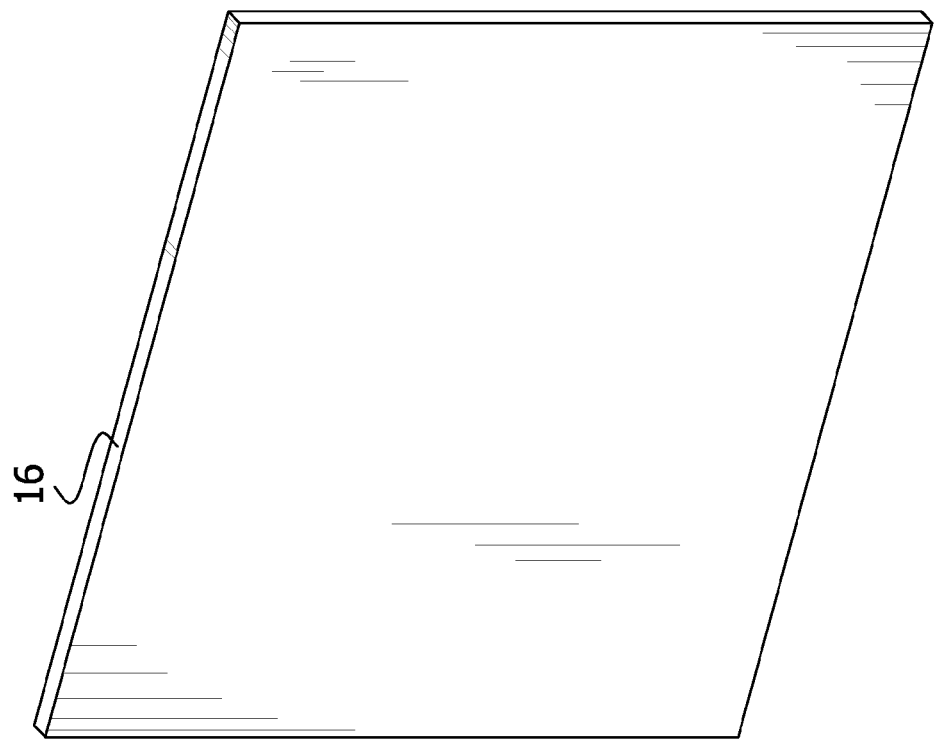
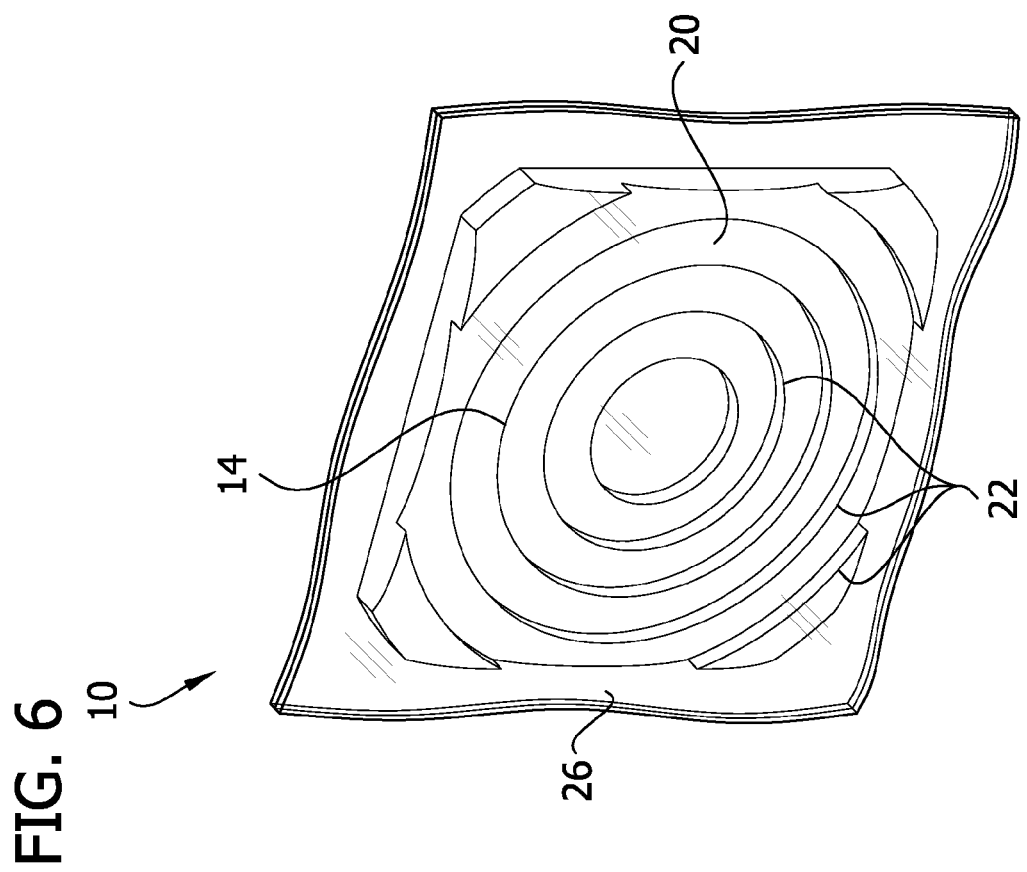
FIG. 6

PHOTOTHERAPY WOUND TREATMENT

FIELD OF THE INVENTION

The present invention generally relates to a wound treatment and, more particularly, to a wound treatment which incorporates a Fresnel lens.

BACKGROUND OF THE INVENTION

It is generally understood that phototherapy treatment of a wound, such as a chronic wound, may facilitate healing of the wound. For example, a phototherapy device may include a laser source to direct light rays to the wound. Current devices uniformly distribute the light rays over the wound. However, there may be some circumstances in which more phototherapy is needed at a center area of the wound or at the perimeter edge margin of the wound. Currently, known phototherapy devices do not provide an easy way to selectively direct light rays toward a specific region of the wound, such as the center region or the perimeter edge margin of the wound.

SUMMARY OF THE INVENTION

In one aspect, a wound treatment for use during phototherapy treatment of a wound generally comprises a pliable optical component adapted to be applied over the wound and to direct light rays passing through the optical component toward a selected area of the wound during phototherapy treatment. A bandage is provided for securing the optical component over the wound.

In another aspect, an optical component for use during phototherapy treatment of a wound is configured to direct light rays toward a perimeter edge of the wound.

In yet another aspect, a wound treatment kit for phototherapy treatment of a wound generally comprises a package, and a sterile, pliable optical component in the package. The optical component is removable from the sterile package and adapted to be placed over the wound during the phototherapy treatment. The optical component is adapted to direct light rays passing through the optical component toward a selected area of the wound during phototherapy treatment.

BRIEF DESCRIPTION OF THE DRAWINGS

FIG. 6 is a example of the wound treatment embodied as a kit;

Corresponding reference characters indicate corresponding parts throughout the drawings.

DETAILED DESCRIPTION OF THE DRAWINGS

Figure 1:
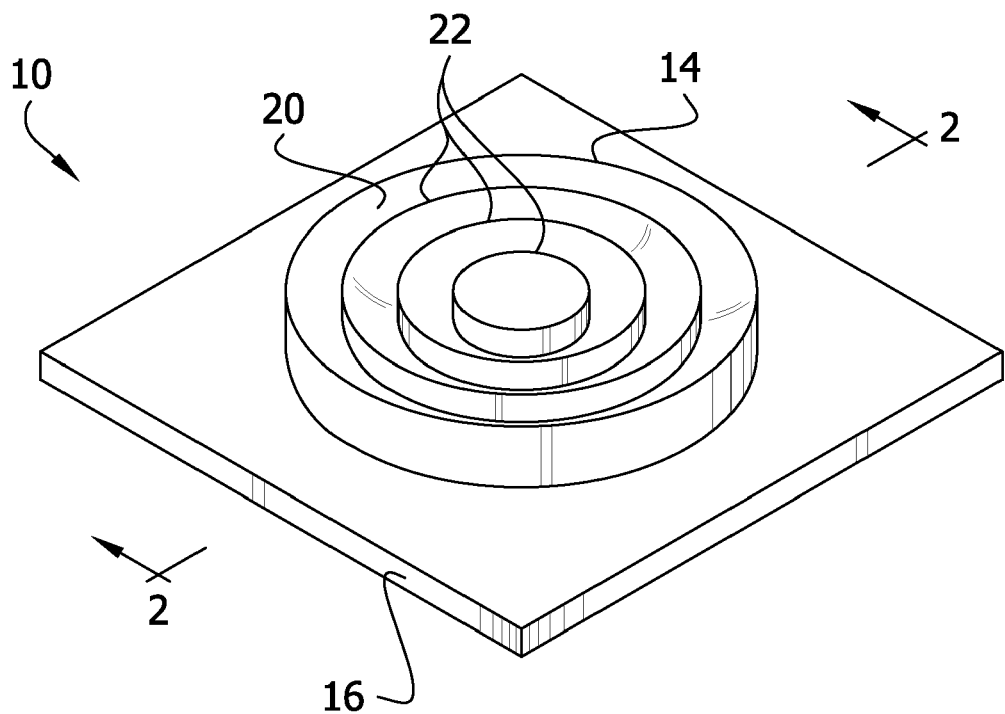
FIG. 1 is a perspective of a first embodiment of a wound treatment of this invention.
Figure 2:
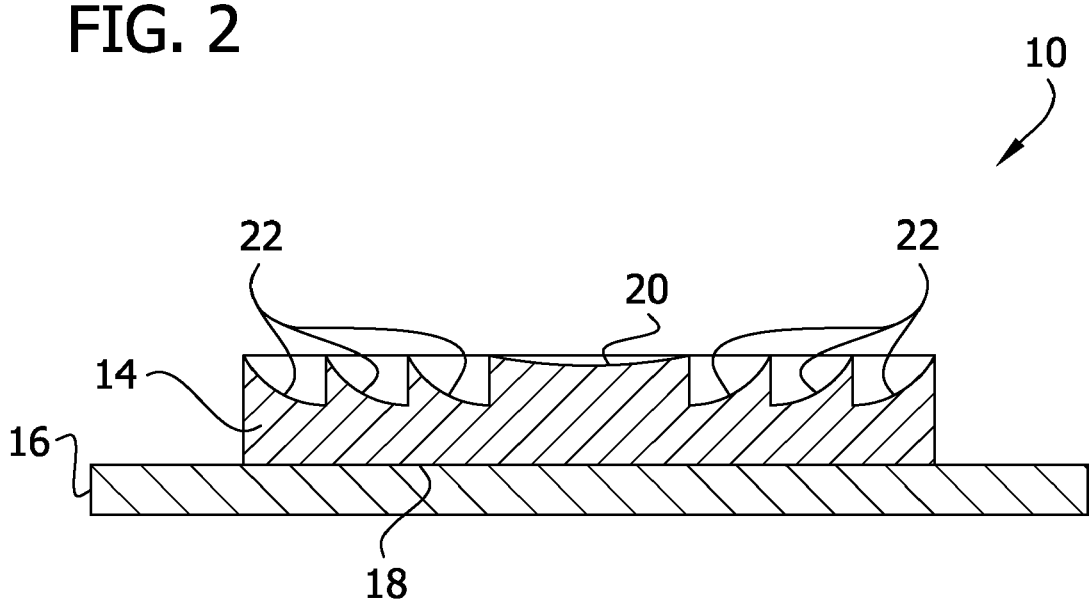
FIG. 2 is a section of the wound treatment taken along the line 2-2 in FIG. 1.
Figure 3:
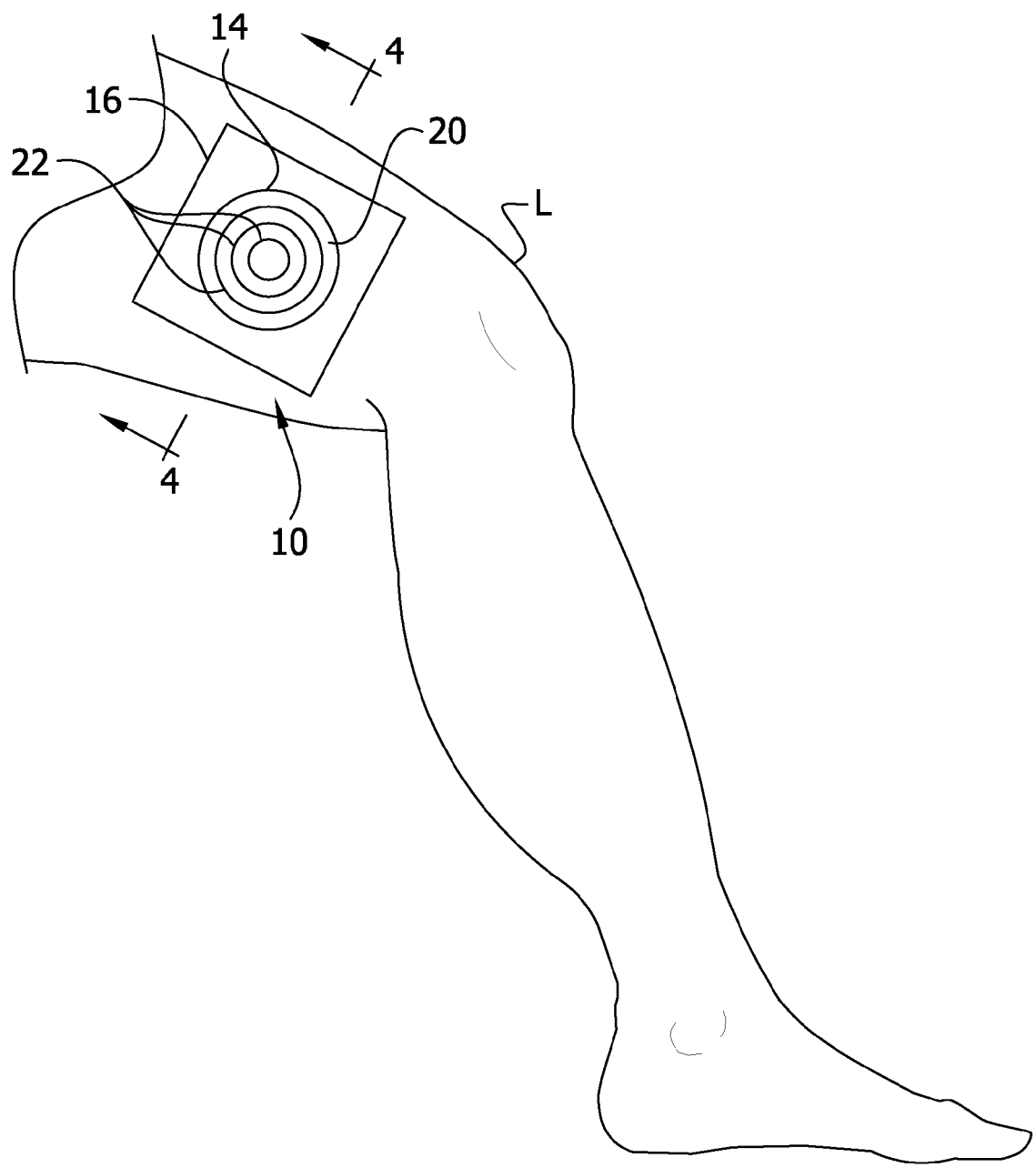
FIG. 3 is a front elevation of the wound treatment secured over a wound on a leg of a patient.

Referring to the drawings, and particularly, to FIGS. 1-4, a first embodiment of a disposable wound treatment for use during phototherapy treatment of a wound is generally indicated at 10. In FIGS. 2 and 3, the wound treatment 10 is shown in a generally bent configuration and adhered over a wound W on a leg L of a patient. In general, the wound treatment 10 comprises a Fresnel lens 14 (broadly, an optical component) adapted to be positioned over and immediately adjacent or in contact with the wound W, and a bandage 16 securing the lens to the patient. It is understood that the wound treatment 10 may include other components in addition to the Fresnel lens 14 and the bandage 16 without departing from the scope of the present invention. Moreover, although the Fresnel lens 14 is shown throughout the drawings as being in direct contact with the wound, it is understood that a separate layer may be disposed between the wound W and the lens without departing from the scope of the present invention. In other words, the Fresnel lens 14 is still considered to be applied over the wound W regardless of whether another layer of wound dressing is between the lens and the wound. For example, a transparent or translucent layer or other layer that allows the transmission of light through it may be in direct contact with the wound W between the lens 14 and the wound.

Referring still to FIGS. 1-4, the transparent Fresnel lens 14 is a diverging Fresnel lens, which, as is known in the art, has a negative focal length. The Fresnel lens 14 has a smooth outer face 18 facing away from the wound, and an inner face 20 having a plurality of annular, concentric lens surfaces 22 facing toward the wound. During phototherapy treatment, light rays from a phototherapy device 24 (FIG. 4), such as a laser, are directed toward the Fresnel lens 14. The Fresnel lens 14 directs (e.g., refracts) the light rays toward a perimeter edge margin E of the wound W. It is believed that the negative Fresnel lens 14 of the first embodiment may be advantageously used during phototherapy treatment to promote tissue growth and healing at the perimeter edge margin E of the wound W. The general configuration of the Fresnel lens 14 necessary to direct light rays toward the perimeter edge margin E of the wound is generally understood by one having ordinary skill in the art. In addition to facilitating phototherapy treatment, the transparent Fresnel lens 14 facilitates visual monitoring of the healing process without removal of the dressing. It is understood that the wound treatment 10 may include other components, including wound dressing, in addition to the Fresnel lens 14 and the bandage 16 without departing from the scope of the present invention.

Figure 4:
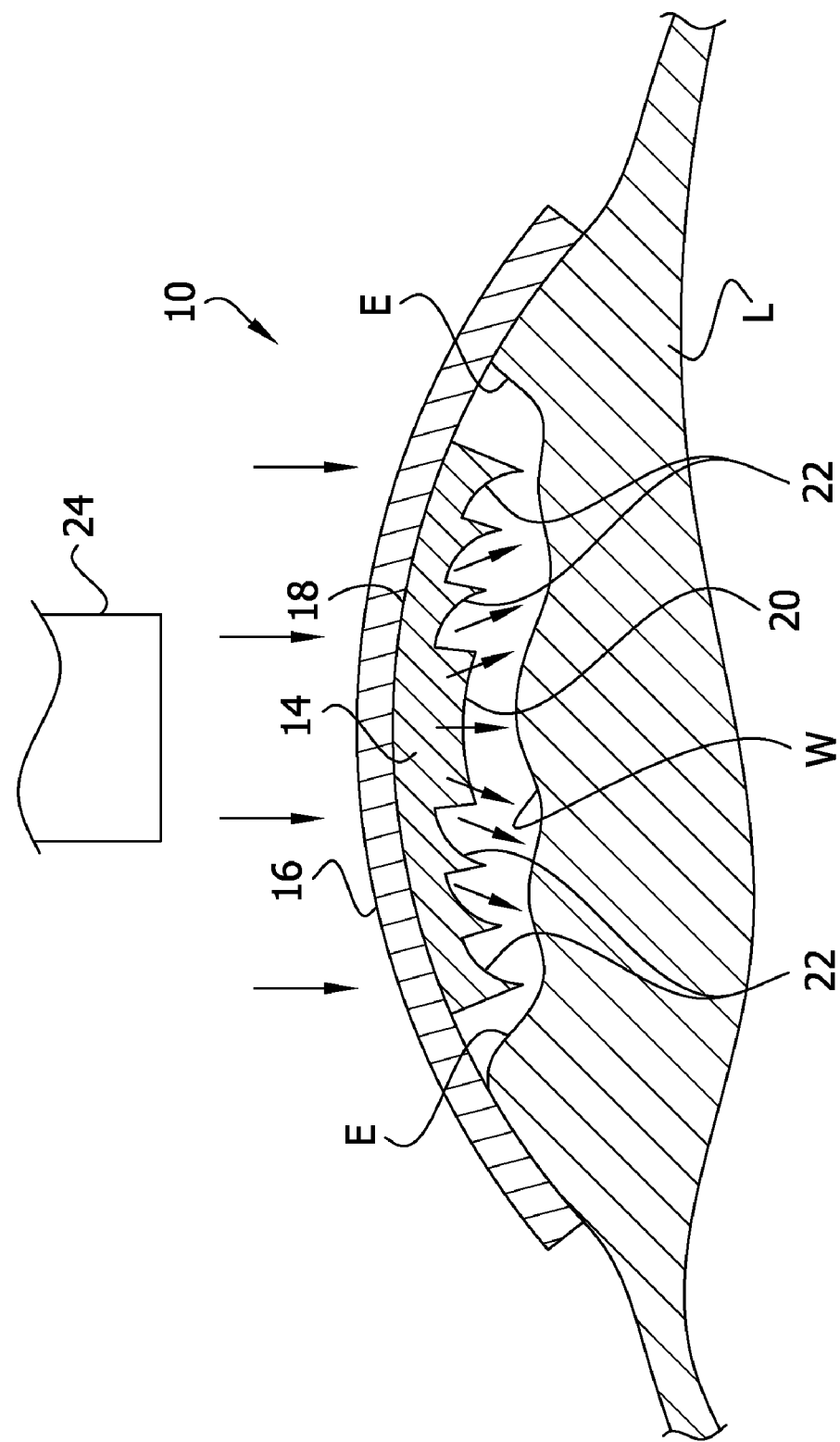
FIG. 4 is a section of the wound treatment and the leg of the patient taken along the line 4-4 in FIG. 3.

In one example, the Fresnel lens 14 may be constructed of a resiliently pliable, transparent material so that the lens can generally conform to the profile of the wound W, as shown in FIGS. 3 and 4. The lens 14 may be generally rigid without departing from the scope of the present invention. The Fresnel lens 14 may also be constructed of a transparent material having a Shore hardness within a range of about 20 A durometer to about 60 A durometer. In one example, the Fresnel lens 14 is constructed of a transparent material having a Shore hardness of about 40 A durometer. The Fresnel lens 14 may be constructed of material having a Shore hardness other than given above without departing from the scope of the present invention. The Fresnel lens 14 may be air-permeable to allow the wound to "breathe", which may facilitate healing. The Fresnel lens 14 may be air-impermeable without departing from the scope of the present invention. The Fresnel lens 14 may also be liquid-permeable to allow the passage of wound exudates through the lens. For example, the lens 14 may have perforations. The Fresnel lens 14 may be water vapor-permeable to allow the passage of water vapor through the lens. For example, the lens 14 may have perforations. The Fresnel lens 14 may be water vapor-impermeable without departing from the scope of the present invention.

The Fresnel lens 14 may be constructed of a PVC-based material, or an acrylic-based material or a silicon-based material that has an elastic modulus within the above-rected elastic modulus range, and/or that has a hardness within the above-recited Shore hardness range. The Fresnel lens 14 may also be formed from material that is air-permeable and/or liquid-permeable, or may be formed in such as way that it is air-permeable and/or liquid-permeable. In one example, the Fresnel lens 14 may be formed by a casting on a textured substrate. The lens 14 may be made in other ways, including but not limited to, molding, extrusion, lithography, and a multi-stage material transfer process. As an example, the lens 14 may be constructed of a urethane-based material. The lens 14 may be formed from other, substantially transparent materials, including laminates thereof. For example and without being limiting, the lens may be constructed of one or more of the following: a polyester-based material, a polyurtethane-based material, a polyolophin-based material, a polypropylene-based material, a silicone-based material, an acrylic-based material, and a styrene-based material.

Figure 5:
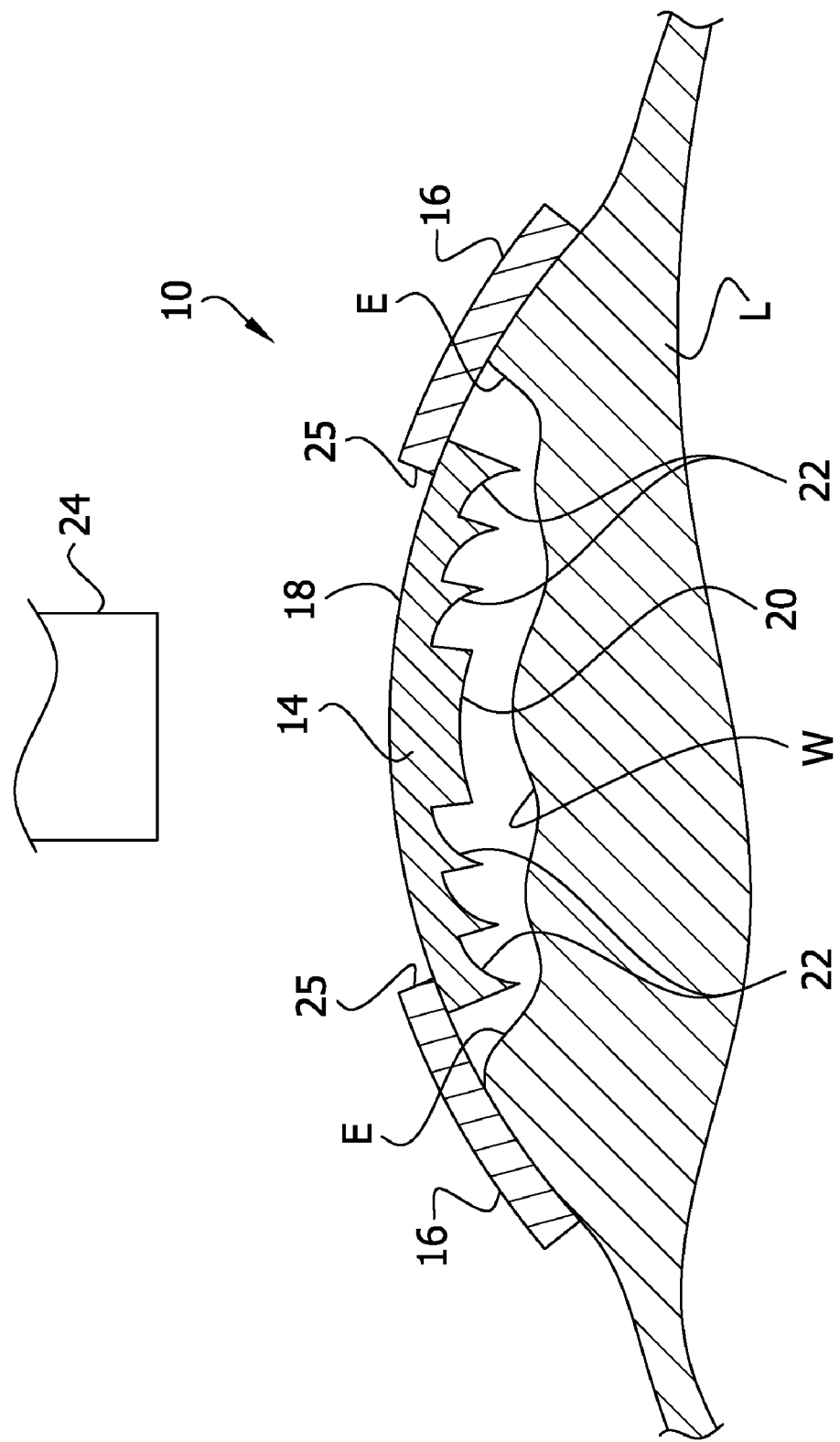
FIG. 5 is a section of an alternative example of the first embodiment similar to FIG. 4.

Referring still to FIGS. 1 and 2, the bandage 6 of the first embodiment is secured to the smooth outer face 18 of the Fresnel lens 14, although it is understood that the bandage may be secured to the inner face 20 without departing from the scope of the present invention. In the first illustrated embodiment, the bandage 16 is formed separate from the Fresnel lens 14 and secured thereto, such as by adhesive or heat welding. Moreover, the bandage 16 covers an entirety of the outer face 18 of the Fresnel lens 14. As such, at least the portion of the bandage 16 covering the outer face 18 of the Fresnel lens 14 is sufficiently transparent to allow light rays to pass through the bandage to the Fresnel lens. It is contemplated that the bandage may not cover the entirety of the outer face 18 of the Fresnel lens, but instead may having an opening 25 exposing a region of the outer face of the lens and a portion surrounding the opening may be secured to the Fresnel lens generally adjacent to the perimeter of the outer face, as shown in FIG. 5, where like components are indicated by corresponding reference numerals. The bandage 16 may include an adhesive material to secure the bandage to the patient. Other ways of securing the bandage to the patient do not depart from the scope of the present invention.

It is contemplated that at least the Fresnel lens 14 is sterile. In one embodiment the wound treatment 10 may be provided to medical personnel as a kit. For example, referring to FIG. 6, the sterile Fresnel lens 14 may be available to medical personnel in a package 26, and the bandage 16 may be sterile and provided in a separate package or may not be provided in a package. It is understood that the Fresnel lens 14 and the bandage 16 may be provided in the same package. In an exemplary use, the Fresnel lens 14 may be applied to the wound W, and then the bandage 16 may be applied over the Fresnel lens to secure the lens over the wound. The bandage 16 may be provided as a sheet (as illustrated) having a circular shape, or an elliptical shape, or a rectangular shape, or a square shape, or other shapes. The bandage 16 may be provided as a continuous strip in roll form without departing from the scope of the present invention.

It is also contemplated that the Fresnel lens 14 of FIG. 6 may be sold as a modular lens that can be sized and shaped by the medical personnel to fit within the wound bed and to generally to conform to the size and shape of the wound W. For example, Fresnel lens 14 may be constructed to be easily shearable (cut or torn) by using scissors or a scalpel or one's hands, so that medical personnel can size and shape the Fresnel lens to conform to substantially any wound. The lens 14 may include indicia indicating a center of the lens to facilitate correct placement of the lens relative to the wound (i.e., with the center of the lens aligned over the center of the wound). The Fresnel lens 14 may have a circular shape, or elliptical shape or a rectangular shape (as shown), or a square shape, or other shapes. It is also contemplated that the Fresnel lens 14 may include perforations or one or more lines of weakness to facilitate shearing of the lens. In another example, the Fresnel lens 14 can be provided in different unalterable sizes and shapes which can be used as needed by medical personnel. In yet another example, the Fresnel lens 14 may sized and shaped to extend over the wound W, but not necessarily in the wound W. In this example, the Fresnel lens would be sized and shaped to contact healthy skin adjacent to the perimeter of the wound bed and extend over the wound W.

Figure 7:
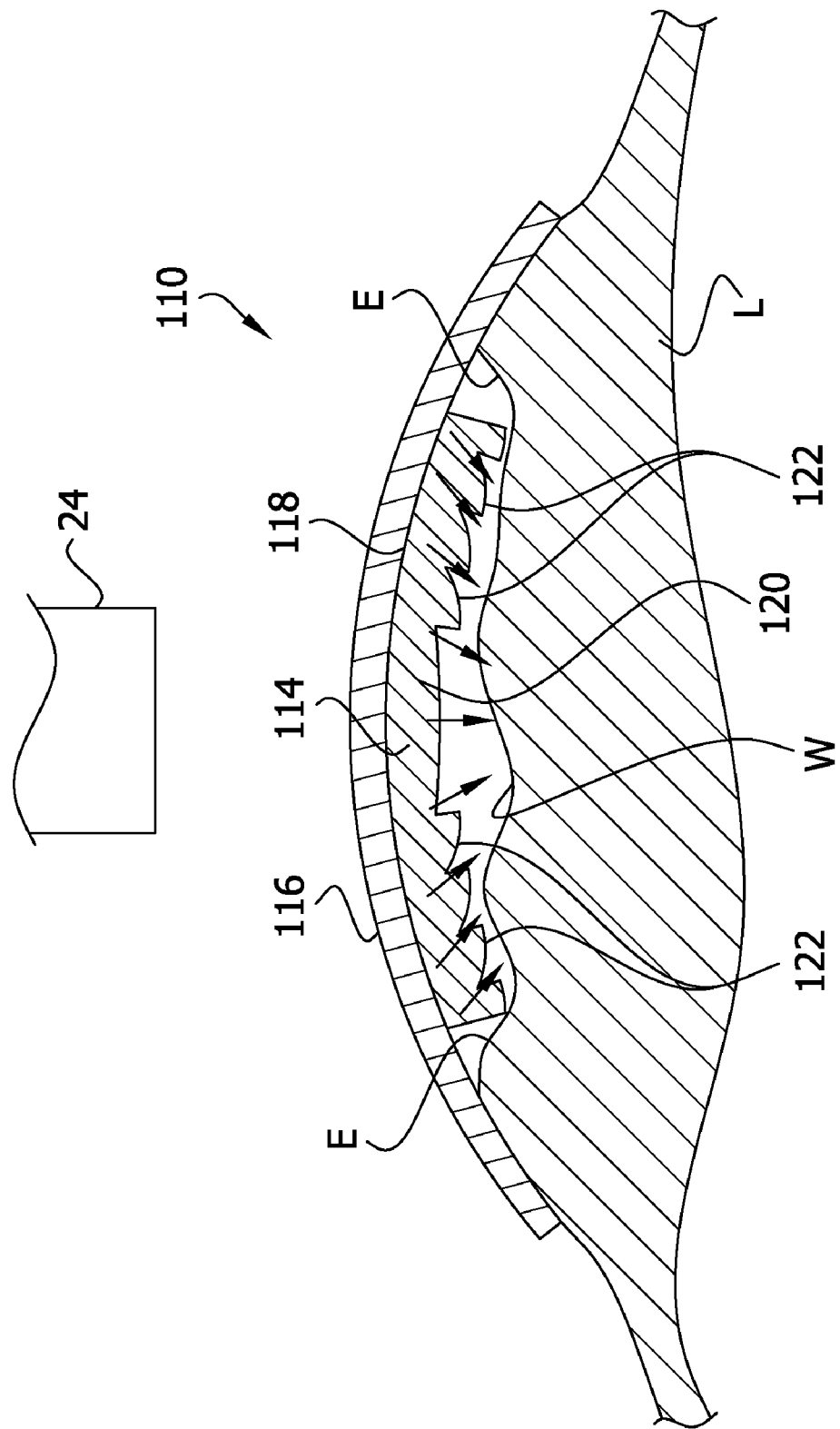
FIG. 7 is a fragmentary section of a second embodiment of a wound treatment adhered over a wound similar to FIG. 2.

Referring to FIG. 7, a second embodiment of the wound treatment is generally indicated at 110. This embodiment is similar to the first embodiment with like components being indicated by corresponding reference numerals plus 100. In the second embodiment, the Fresnel lens 114 (broadly, the optical component) is a converging Fresnel lens having a positive focal length. During phototherapy treatment, the Fresnel lens 114 directs (e.g., refracts) light rays toward a center region of the wound W. It is believed that the converging Fresnel lens 114 of the second embodiment may be advantageously used during phototherapy treatment to promote tissue growth and healing at the center region of the wound W. The general configuration of the Fresnel lens 114 necessary to direct light rays toward the center region of the wound W, including the size and shape of the lens surfaces 122, is generally understood by one having ordinary skill in the art. It is understood that the Fresnel lens 114 may include other components, including a wound dressing, without departing from the scope of the present invention. It is contemplated that the bandage 116 may not cover the entire smooth outer face 118 of the Fresnel lens 114, but instead may be secured to the Fresnel lens generally adjacent to the perimeter of the outer face to expose a majority of the outer face, similar to FIG. 5. Other ways of securing the bandage 116 to the Fresnel lens 114 do not depart from the scope of the present invention.

Figure 8:
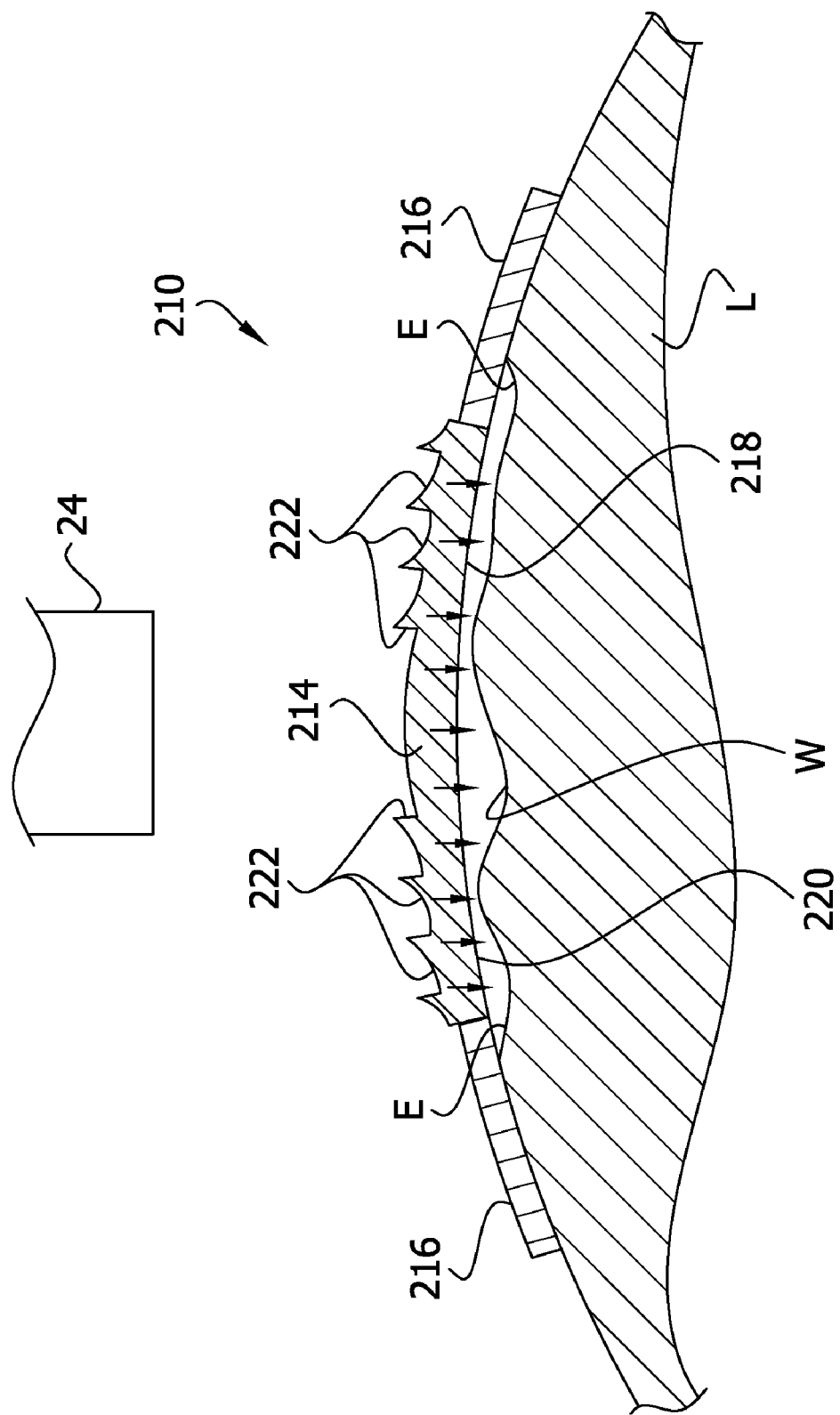
FIG. 8 is a fragmentary section of a third embodiment of a wound treatment adhered over a wound similar to FIG. 2.

Referring to FIG. 8, a third embodiment of the wound treatment is generally indicated at 210. This embodiment is similar to the first embodiment with like components being indicated by corresponding reference numerals plus 200. The Fresnel lens 214 (broadly, the optical component) of the third embodiment is a positive Fresnel lens, similar to the Fresnel lens 14 of the first embodiment. The difference between the lenses is that the Fresnel lens 214 of the third embodiment is rotated 180 degrees relative to the lens 14 of the first embodiment so that an inner face 220 that contacts the wound W is generally smooth and the outer face 218 has annular lens surfaces 222. In addition, the bandage 216 is secured to the perimeter edge margin of the Fresnel lens 214, although it is understood that the bandage 216 may cover either the lens surfaces 222 of the outer face 218 or the smooth inner face 220 without departing from the scope of the invention. Other ways of securing the bandage 216 to the Fresnel lens 214 do not depart from the scope of the present invention.

The Fresnel lens 214 functions as a collimator in that diverging light rays from a phototherapy device 24 collimate or become parallel as the rays pass through the lens. Because the Fresnel lens 214 collimates the light rays, a generally uniform distribution of light rays can be directed on the wound W. Moreover, the phototherapy device 24 (i.e., the light ray source) can be located closer to the wound W when using the collimating lens 214 than when using the other lenses 14, 114 or no lens. As a result, it is believed that the required output intensity for the phototherapy device may be reduced when using the collimating lens 214 because the phototherapy device can be placed closer to the wound W than if the lens did not collimate the light rays.

Figure 9:
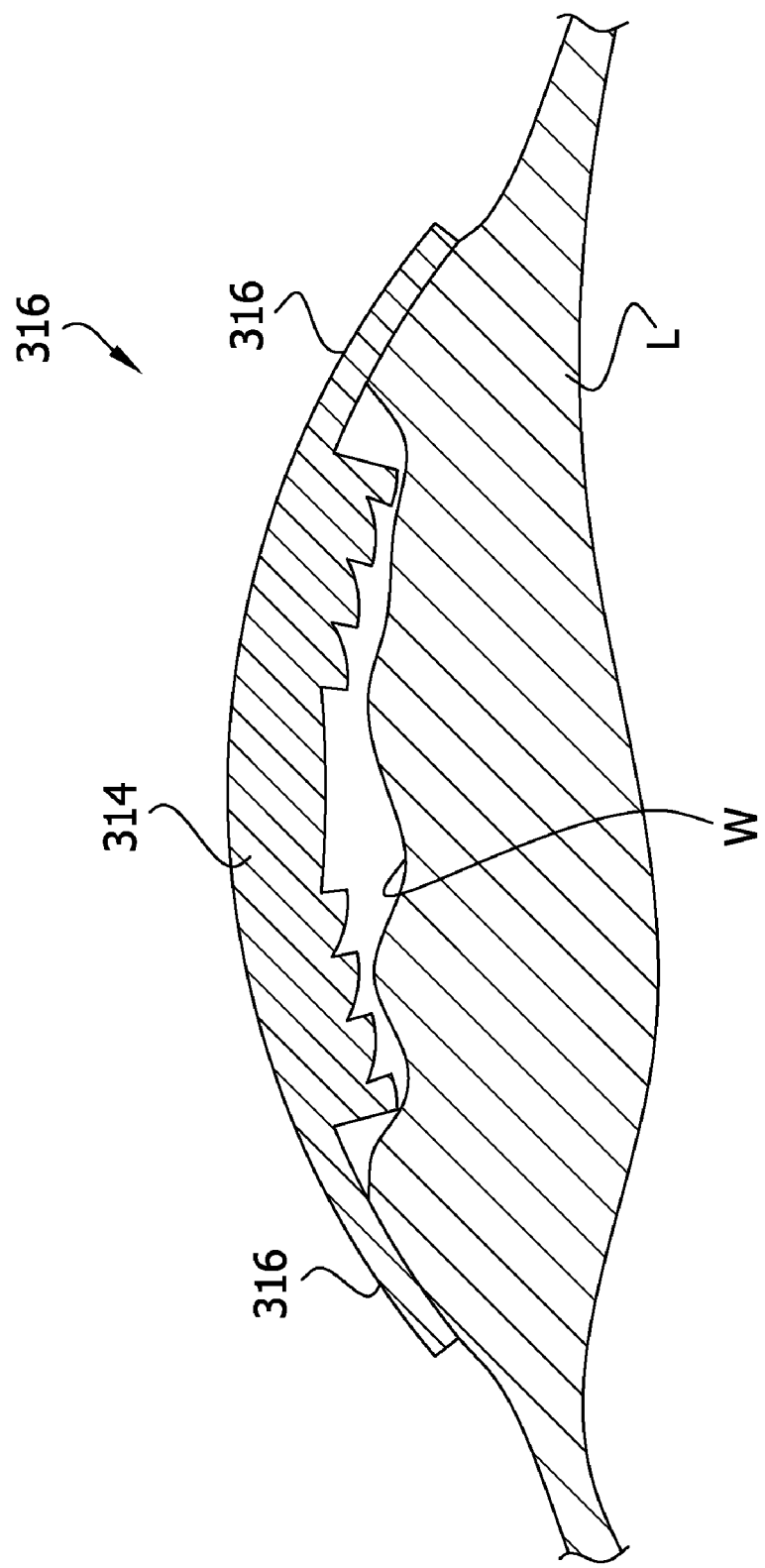
FIG. 9 is a fragmentary section of a fourth embodiment of a wound treatment adhered over a wound similar to FIG. 2.

Referring to FIG. 9, a fourth embodiment of the wound treatment is generally indicated at 310. This embodiment is similar to the first embodiment with like component being indicated by corresponding reference numerals plus 300. In the fourth embodiment, the Fresnel lens 314 (broadly, the optical component) and the bandage 316 are integrally formed as a single part. For example, the wound treatment 310 may be molded so that the bandage 316 comprises wings extending laterally outward from the Fresnel lens 314. Although this embodiment includes a diverging Fresnel lens 314, it is understood that other types of Fresnel lenses, including any of the lenses described herein, may be used.

Figure 10:
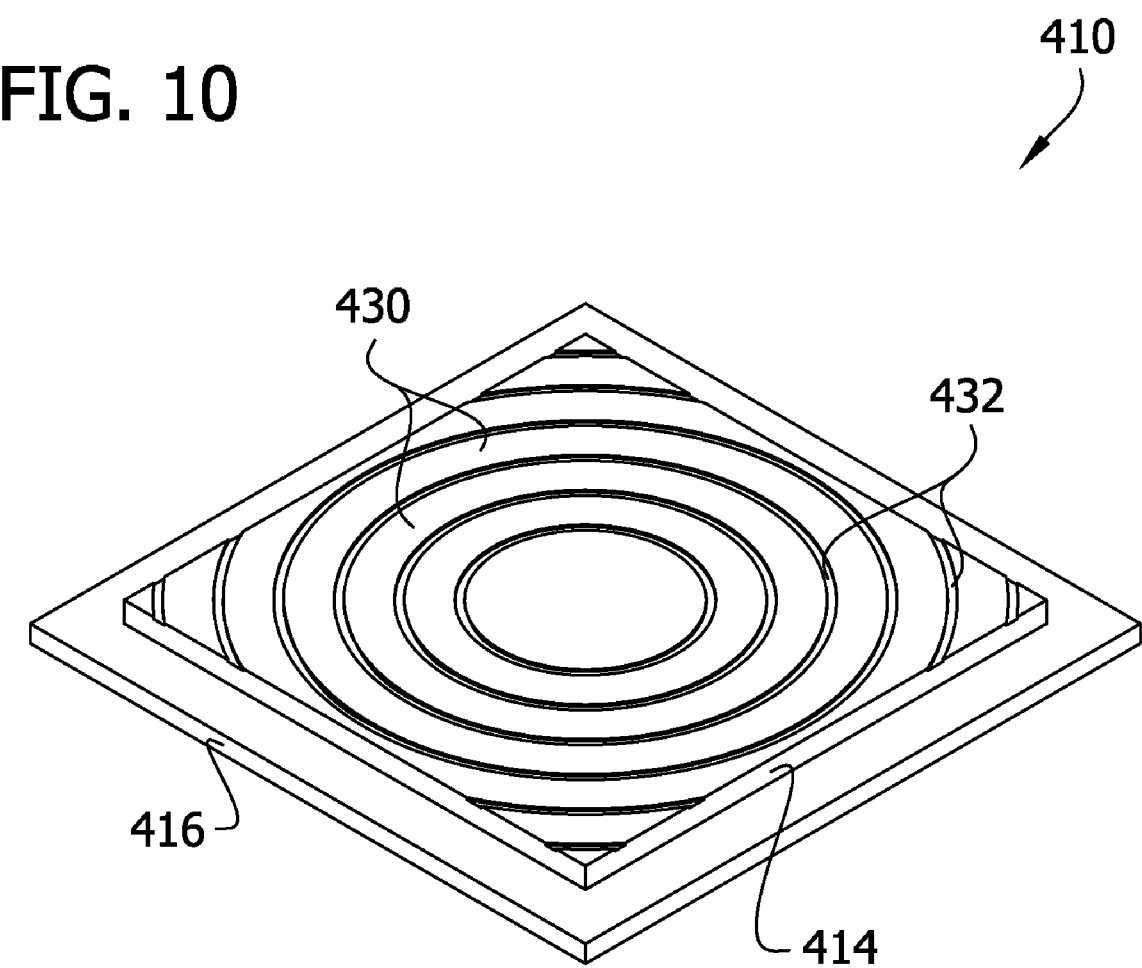
FIG. 10 is a perspective of a fifth embodiment of a wound treatment of this invention.

Referring to FIG. 10, a fifth embodiment of the wound treatment is generally indicated at 410. This embodiment is similar to the first embodiment of FIGS. 1-4, except that the wound treatment 410 includes a diffraction grating 414 (broadly, an optical component), secured to a bandage 416, instead of a Fresnel lens. The diffraction grating 414 has concentric and alternating non-transmitting and narrow transmitting annular areas 430, 432, respectively. The non-transmitting annular areas 430 do not allow light to pass through the grating 414, while the transmitting annular areas 432 allow for light to pass therethrough. The size and spacing of the non-transmitting and transmitting areas 430, 432 are shown for ease of illustration. One of ordinary skill in the art would understand how to size and space these areas to produce the desired light directing affect. Through this configuration, light passing through the narrow transmitting areas 432 diffract, as with any diffraction grating. For example and without being limiting, the non-transmitting areas 430 may be opaque and the transmitting areas 432 may be transparent. In another example, the transmitting areas 432 may be slits. Other configurations of the diffraction grating 414 do not depart from the scope of the invention.

Through diffraction, the diffraction grating 414 is configured to direct light rays (just as for the phototherapy device 24 shown in FIG. 4) toward a selected area of the wound W, such as toward the perimeter edge margin E of the wound, or toward a center region of the wound W, or toward an entirety of the wound W. The diffraction grating 414 may be at least one of air-permeable and liquid-permeable and water vapor-permeable. Moreover, the wound treatment 410 may be similar to the other embodiments disclosed herein with the exception that the Fresnel lens is replaced by a suitable diffraction grating 414.

It is understood that other optical components, other than the Fresnel lens and the diffraction grating, may be used to direct light rays passing through the optical component toward a selected area of the wound during phototherapy treatment without departing from the scope of the present invention.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A phototherapy wound treatment device, comprising:
   a bandage having an adhesive on a skin-contacting surface thereof; and
   a pliable optical component secured to the bandage, the pliable optical component comprising a vapor permeable Fresnel lens configured to direct light rays entering an outer face thereof and exiting from a skin-facing inner face thereof toward a perimeter area of the wound.

2. The phototherapy wound treatment device according to claim 1, wherein the pliable optical component is secured to the bandage by an adhesive.

3. The phototherapy wound treatment device according to claim 1, wherein the bandage covers at least a portion of the outer face of the pliable optical component.

4. The phototherapy wound treatment device according to claim 1, wherein at least a portion of the bandage covering the outer face of the pliable optical component is transparent.

5. The phototherapy wound treatment device according to claim 1, wherein the bandage is secured to the outer face of the pliable optical component.

6. The phototherapy wound treatment device according to claim 1, wherein the bandage includes an opening extending therethrough, the pliable optical component being secured to the bandage adjacent a perimeter of the opening.

7. The phototherapy wound treatment device according to claim 6, wherein at least a portion of the outer face of the pliable optical component is exposed by the opening.

* * * * *